United States Patent [19]
Nantz et al.

[11] Patent Number: 5,527,928
[45] Date of Patent: Jun. 18, 1996

[54] CATIONIC TRANSPORT REAGENTS

[76] Inventors: Michael H. Nantz, Department of Chemistry, Univ. or California; Michael J. Bennett, 4849 El Cemonte Ave., #163; Robert W. Malone, 1016 Bienville St., all of Davis, Calif. 95616

[21] Appl. No.: 316,719

[22] Filed: Sep. 30, 1994

[51] Int. Cl.$^6$ .................................................. C07C 229/30
[52] U.S. Cl. ..................... 554/105; 560/179; 560/180; 560/190; 564/511
[58] Field of Search .......................... 554/105; 514/560; 560/179, 180, 190; 564/511

[56] References Cited

U.S. PATENT DOCUMENTS

| | | | |
|---|---|---|---|
| 4,812,449 | 3/1989 | Rideout | 514/183 |
| 5,171,678 | 12/1992 | Behr et al. | 435/172.3 |
| 5,186,923 | 2/1993 | Piwnica-Worms et al. | 424/9 |
| 5,208,036 | 5/1993 | Eppstein et al. | 424/450 |
| 5,264,618 | 11/1993 | Felgner et al. | 560/224 |
| 5,277,897 | 1/1994 | Piwnica-Worms et al. | 424/1.65 |
| 5,279,833 | 1/1994 | Rose | 424/150 |
| 5,334,761 | 8/1994 | Gebeyehu | 564/197 |

FOREIGN PATENT DOCUMENTS 2132196  5/1990  Japan.

OTHER PUBLICATIONS

"Hydrophobic domain of cationic lipids influence respiratory epithial cell DNA transfection," Balasubramaniam, R. P. et al. Manuscript in Preparation, 1994.
Reiner et al., Arzneim. Forsch., 23, No. 8, 1973.
Youji Huaxne, 1990, 10, 464–70.

*Primary Examiner*—Shailendra Kumar
*Attorney, Agent, or Firm*—James M. Ritchey

[57] ABSTRACT

For use in transporting biologically active species into and through membrane barriers, a symmetrical cationic diamine compound having the general structure

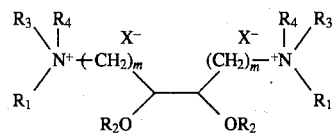

4 Claims, 8 Drawing Sheets

CATIONIC TRANSPORT REAGENTS

BACKGROUND OF THE INVENTION

1. Field of the Invention

Provided are cationic lipids that bind and transport polynucleotides, polypeptides, pharmaceutical substances and other biologically active species through membrane barriers. More specifically, symmetrical diamine cationic lipids are disclosed that complex with selected molecular species and facilitate delivery of those selected species into and through membranes and comparable boundary structures.

2. Description of the Background Art

Cellular transfection strategies for gene therapy and similar goals have been designed and performed, but many of these procedures involve recombinant virus vectors and various problems exist with these viral gene transfer systems. Even generally advantageous adenovirus techniques encounter difficulties since most humans have antibodies to many of the adenovirus serogroups, including those that have been chosen as vectors. Wild type adenoviral superinfection of an adenoviral vector treated patient may result in propagating the recombinant vector as a defective viral particle, with the ability to infect many unintended individuals (if chosen to have a rare serogroup). The chance of adenoviral contamination is quite low but not impossible. The safety of using these genetic materials in humans remains unclear and thus hazardous.

Safe, non-viral vector methods for transfection or gene therapy are essential. A few such safe lipid delivery systems for transporting DNA, proteins, and other chemical materials across membrane boundaries have been synthesized by research groups and business entities. Most of the synthesis schemes are relatively complex and generate transporters having only limited transfection abilities. A need exists in the field of cationic lipid transporters for cationic species that have a high biopolymer transport efficiency. It has been known for some time that quaternary ammonium derivatized (cationic)liposomes spontaneously associate with DNA, fuse with cell membranes, and deliver the DNA into the cytoplasm. LIPOFECTIN™ represents a first generation of cationic liposome formulation development. LIPOFECTIN™ is composed of a 1:1 formulation of the quaternary ammonium containing compound DOTMA and dioleoylphosphatidylethanolamine sonicated into small unilamellar vesicles in water. One problem with LIPOFECTIN™ is that it contains non-metabolizable ether bonds. Other problems with LIPOFECTIN™ are an inhibition of protein kinase C activity and direct cytotoxicity. In response to these problems, a number of other related compounds have been developed. The diamine compounds of the subject invention improve upon the capabilities of existing cationic transporters and serve as very efficient delivery means for biologically active chemicals.

As indicated immediately above, various cationic lipids have been synthesized in previous references. For example, U.S. Pat. No. 4,812,449 discloses in situ active compound assembly of biologically active agents at target locations in preference to surroundings which are desired to be unaffected. Several charged and uncharged amine derivatives are described.

Introduced in U.S. Pat. No. 5,171,678 are lipopolyamines and their use for transfecting eukaryotic cells. A polynucleotide is mixed with the subject lipopolyamine and contacted with the cells to be treated.

U.S. Pat. Nos. 5,186,923 and 5,277,897 relate an enhancement of cellular accumulation of lipophilic cationic organometallic compounds by reduction of the intramembrane potential. Technetium containing compounds are disclosed.

Lipophilic cationic compounds are presented in U.S. Pat. No. 5,208,036. Asymmetrical amine compounds are synthesized and employed in a method for DNA transfection.

U.S. Pat. No. 5,264,618 discloses cationic lipids for intracellular delivery of biologically active molecules. Asymmetric ammonium containing cationic lipids are presented for transporting molecules into membranes enclosed systems.

Transfection of nucleic acids into animal cells via a neutral lipid and a cationic lipid is revealed in U.S. Pat. No. 5,279,833. Liposomes with nucleic acid transfection activity are formed from the neutral lipid and the ammonium salt containing cationic lipid.

U.S. Pat. No. 5,334,761 describes other amine containing cationic lipids are reported. Cationic lipids are utilized to form aggregates for delivery of macromolecules and other compounds into cells.

The foregoing patents reflect the state of the art of which the applicants are aware and are tendered with the view toward discharging applicants' acknowledged duty of candor in disclosing information which may be pertinent in the examination of this application. It is respectfully submitted, however, that none of these patents teach or render obvious, singly or when considered in combination, applicants' claimed invention.

SUMMARY OF THE INVENTION

An object of the present invention is to disclose a category of diamines that greatly facilitate the delivery of biologically active compounds through membrane structures.

Another object of the present invention is to present a group of symmetrical diamine cationic compounds that assist in the transport of selected macromolecules and other substances into and past membrane barriers.

A further object of the present invention is to relate a collection of biologically active molecule transporters having easily variable lipid components linked to a symmetrical polyhydroxyl containing diamine core structure.

Disclosed are novel diamine cationic transporter molecules that facilitate the delivery of such compounds as polynucleotides, polypeptides, and the like into and beyond membrane walls. Generally related are symmetrically structured cationic diamines, either polyhydroxylated or otherwise quaternized, having at least a pair of identical lipoyl moieties selected from a group consisting of an alkyl chain, an alkenyl chain, and an alkyl or alkenyl containing acyl chain. More specifically, a compound having the structure:

wherein m=1–10; $R_1$ is a hydrogen, an alkyl group, an alkenyl group, or a hydroxylated alkyl or alkenyl group; $R_2$ is an alkyl group, an alkenyl group, or an alkyl or alkenyl containing acyl group; $R_3$ is a hydrogen, an alkyl group, an alkenyl group, or a hydroxylated alkyl or alkenyl group; $R_4$ is a hydrogen, an alkyl group, an alkenyl group, or a hydroxylated alkyl or alkenyl group; and $X^{31}$ is an anion.

In particular, a preferred composition is N,N,N', N'-tetramethyl-N,N'-bis (2-hydroxyethyl)-2,3-di(oleoyloxy)-1,4-butanediaminium iodide, given the nickname PolyGum in view of its binding affinity. Even though this is a preferred composition, the length and double bond characteristics of the $R_2$ group (as is detailed below) and the presence or absence of a carbonyl in the $R_2$ group is variable.

Other objects, advantages, and novel features of the present invention will become apparent from the detailed description that follows, when considered in conjunction with the associated drawings.

DESCRIPTION OF THE PREFERRED EMBODIMENT

Referring now to the following disclosure and to the data presented in FIGS. 1–8, there is described a preferred embodiment of a symmetrical cationic diamine having at least a pair of identical lipoyl moieties selected from a group consisting of an alkyl chain, an alkenyl chain, and an alkyl or alkenyl containing acyl chain.

Generally, the diamine is polyhydroxylated and has a generalized structure of:

wherein m=1–10, preferably 1; $R_1$ is a hydrogen, an alkyl group, an alkenyl group, or a hydroxylated alkyl or alkenyl group; $R_2$ is an alkyl group, an alkenyl group, or an alkyl or alkenyl containing acyl group; $R_3$ is a hydrogen, an alkyl group, an alkenyl group, or a hydroxylated alkyl or alkenyl group; $R_4$ is a hydrogen, an alkyl group, an alkenyl group, or a hydroxylated alkyl or alkenyl group; and $X^-$ is an anion. The extra, with m more than 1, number of methylenes is introduced by standard procedures that complement the described subject synthetic pathways.

More specifically, the structure is:

wherein for compound 1: n=0–10, usually between 0 and 3, preferably 1; $R_1$ is a hydrogen, an alkyl group, an alkenyl group, or a hydroxylated alkyl or alkenyl group, generally having from 1 to 10 preferably 1 carbon; $R_2$ is an alkyl group, an alkenyl group, or an alkyl or alkenyl containing acyl group; $R_3$ is a hydrogen, an alkyl group, an alkenyl group, or a hydroxylated alkyl or alkenyl group, often an alkyl group of from 1 to 10 carbons, preferably a methyl group; and $X^-$ is an anion, usually a halide, and preferably iodide.

To facilitate discussing the subject compounds, a list of abbreviations, nicknames, or acronyms follows:

| | |
|---|---|
| DC Cholesterol | 3β-[N-(N',N'-dimethylaminoethane)-carbamoyl] cholesterol |
| DCPE | Dicaproylphosphatidylethanolamine |
| DMAP | 4-Dimethylaminopyridine |
| DMEM | Dulbecco's modified Eagles medium |
| DMPE | Dimyristoylphosphatidylethanolamine |
| DOGS | Dioctadecylamidoglycyl spermidine |
| DOHME | N-[1-(2,3-dioleoyloxy)propyl]-N-[1-(2-hydroxyethyl)]-N,N-dimethylammonium iodide |
| DOPE | Dioleoylphosphatidylethanolamine |
| DOSPA | 2,3-Dioleoyloxy-N-[2-(sperminecarboxamido)ethyl]-N,N-dimethyl-1-propanaminium trifluoroacetate |
| DOTAP | N-[1-(2,3-dioleoyloxy)propyl]-N,N,N-trimethylammonium iodide [DIESTER] (Boehringer Mannheim GmbH) |
| DOTMA | N-[1-(2,3-dioleyloxy)propyl]-N,N,N-trimethylammonium bromide [DIETHER] |
| DSPE | Distearoylphosphatidylethanolamine |
| DU-145 | Human prostatic carcinoma cells for a representative human tumor cell line |
| FBS | Fetal Bovine Serum |
| Lipofectamine | DOSPA + DOPE |
| Lipofectin Reagent | DOTMA + DOPE (Vical Inc.) |
| NIH 3T3 | Murine fibroblast cells for a representative human cell line |
| MLV | Multilamellar vesicles |
| PE | Phosphatidylethanolamine |
| PolyGum | N,N,N',N'-tetramethyl-N,N'-bis(2-hydroxy-ethyl)-2,3-di(oleoyloxy)-1,4-butane-diaminium iodide |
| SV | Sonicated or extruded vesicles |
| Transfectam Reagent | DOGS |

Although other possible methods of synthesizing the subject compounds are possible, a preferred and general synthetic scheme for cationic diamine compounds is:

Generalized Synthesis Scheme

General Precursor Compound where: n=1–10; $R_1$ is a hydrogen, an alkyl group, an alkenyl group, or a hydroxylated alkyl or alkenyl group; $R_2$ is an alkyl group, an alkenyl group, or an alkyl or alkenyl containing acyl group; $R_3$ is a hydrogen, an alkyl group, an alkenyl group, or a hydroxylated alkyl or alkenyl group; and X is a halide.

In the general synthesis scheme the first step involves reacting a tert-butyldiphenylsilyloxy derivatized starting material with 1,3-butane diepoxide in the presence of lithium perchlorate in absolute ethanol. The second step is a reaction with an alkyl or alkenyl halide or an alkyl or alkenyl containing acyl halide. The third step is tetrabutylammonium fluoride and THF initiated removal of the tert-butyldiphenylsilyloxy protection groups to produce the general precursor compound. The general precursor compound is then allowed to react with a selected alkyl, alkenyl, or hydroxylated alkyl or alkenyl halide.

More preferred, the subject composition has the structure:

wherein R is an alkyl or alkenyl group, preferably —$CH_2(CH_2)_6CH=CH(CH_2)_7CH_3$ and $X^-$ is an anion, preferably a halide such as iodide. A preferred species of the subject invention, having the name N,N,N',N'-tetramethyl-N,N'-bis(2-hydroxyethyl)-2,3-di(oleoyloxy )-1,4-butanediaminium iodide, has the following structure:

A synthesis scheme for the preferred compound is as follows:

Specific Synthesis Scheme

-continued
Specific Synthesis Scheme

Rationale for Variations in Hydrophobic Domain

As seen in preferred compound, PolyGum, the long lipid tails are both oleoyl groups, however, other lipid tails are acceptable and within the realm of this disclosure. A study (Balasubramaniam, R. P., Bennett, M. J., Gruenert, D., Malone, R. W., and Nantz, M. H., "Hydrophobic Domain of Cationic Lipids Influence Respiratory Epithelial Cell DNA Transfection" manuscript in preparation., which is herein incorporated by reference) involving cationic lipids, which contain a N,N-dimethyl-N-(2-hydroxyethyl) ammonium group [(CH$_3$)$_2$(HOCH$_2$CH$_2$-)N+-R] as the hydrophilic domain (polar head group component present in PolyGum) and which contain various fatty acid combinations to comprise the hydrophobic domain, has shown that subtle changes in the composition of the hydrophobic domain do affect the performance of these lipids as mediators of polynucleotide delivery into mammalian cells (transfection). However, in all examples, the cationic lipids showed activity as agents for polynucleotide transfection. Therefore, the various combinations of fatty acid side chains represent only analogous changes in the overall structure of the cationic lipid, and in each case the cationic lipid is apt to demonstrate transfection activity.

The derivatization of DOHME (a cationic asymmetric lipid containing a mono-ammonium head group) involving changes in the hydrophobic domain has led to the discovery that all the derivatives display transfection activity, yet in varying amounts. By analogy, changes in the hydrophobic domain of PolyGum will lead to new lipids which possess transfection activity. Additionally, this expectation is supported by recent literature work (Felgner, P. L. et al J.  Biological Chem. 1994, 269, 2550) which demonstrates that changes in the hydrophobic domain relative to a constant polar head group affords compounds which exhibit transfection activity to varying degrees.

Figure 1:
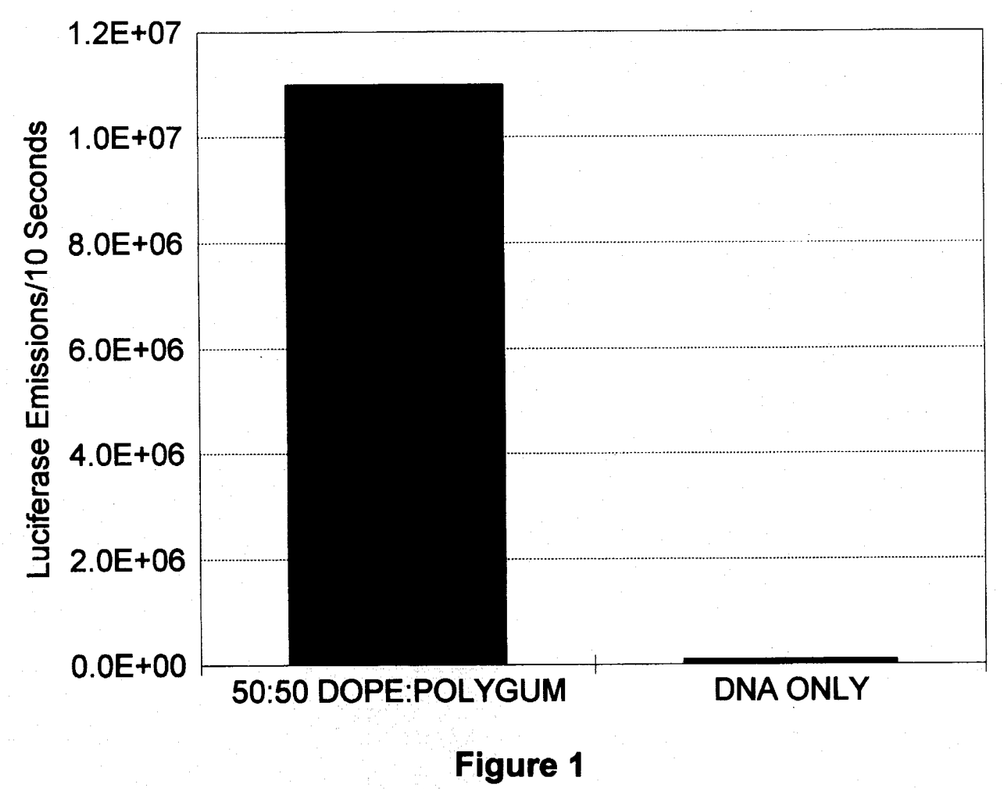
FIG. 1 is a graph that demonstrates the effectiveness of a 50:50 mixture of DOPE:PolyGum with DNA, compared with DNA only, in transfecting NIH 3T3 cells in a serum-free environment.

Transfection or membrane penetration is demonstrated by incorporating the subject diamines into various liposome/DNA complexes and exposing cells under desired conditions to initiate transfection. As seen in FIG. 1, with effectiveness determined by luciferase light emissions (the luciferase plasmid pCMVL, see below, was utilized in a standard manner to detect transfection levels), a serum-free 50:50 DOPE:PolyGum SV very efficiently, as compared with DNA only, mediated DNA transfection of NIH 3T3 cells.

Figure 2:
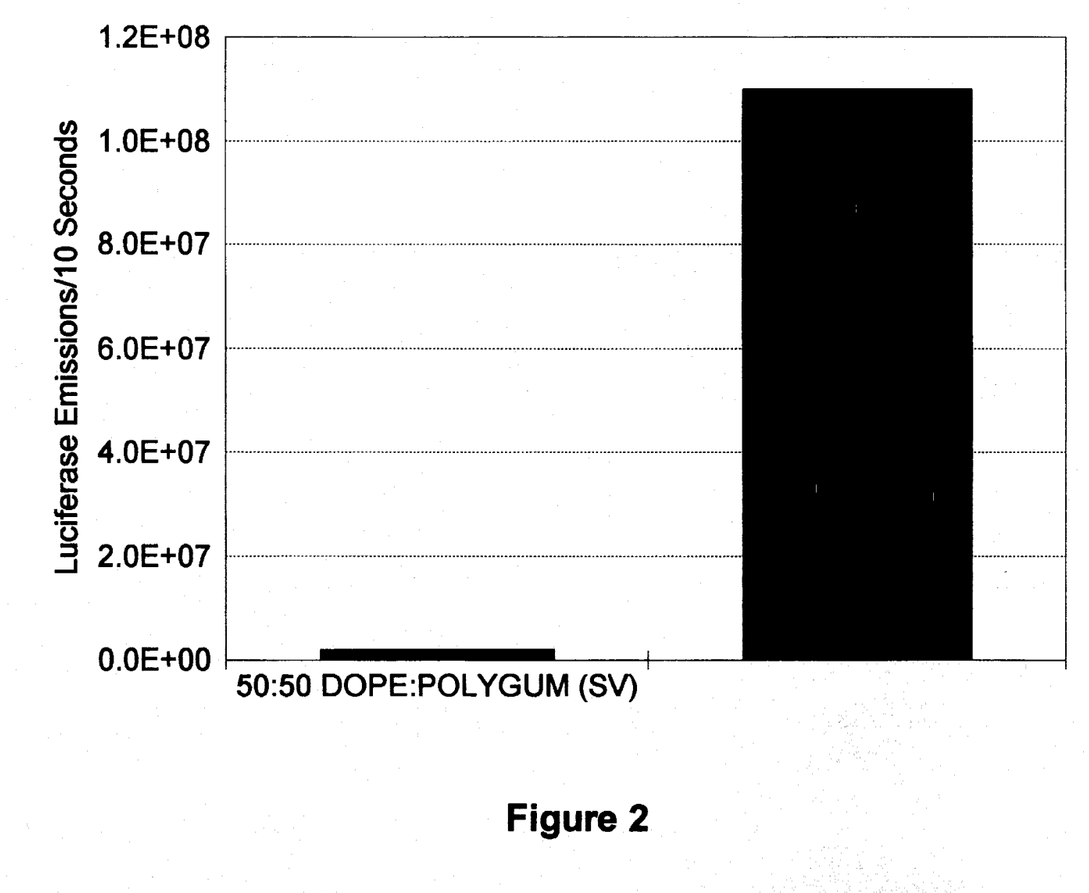
FIG. 2 is a graph that illustrates that liposome structure (SV versus MLV forms) influences the efficiency of transfecting NIH 3T3 cells.

The structural nature of the transfection vesicle influences the efficiency of the transfection. FIG. 2 clearly indicates that with a 50:50 DOPE:PolyGum formulation, the SVs are much more capable transfection carriers.

Figure 3:
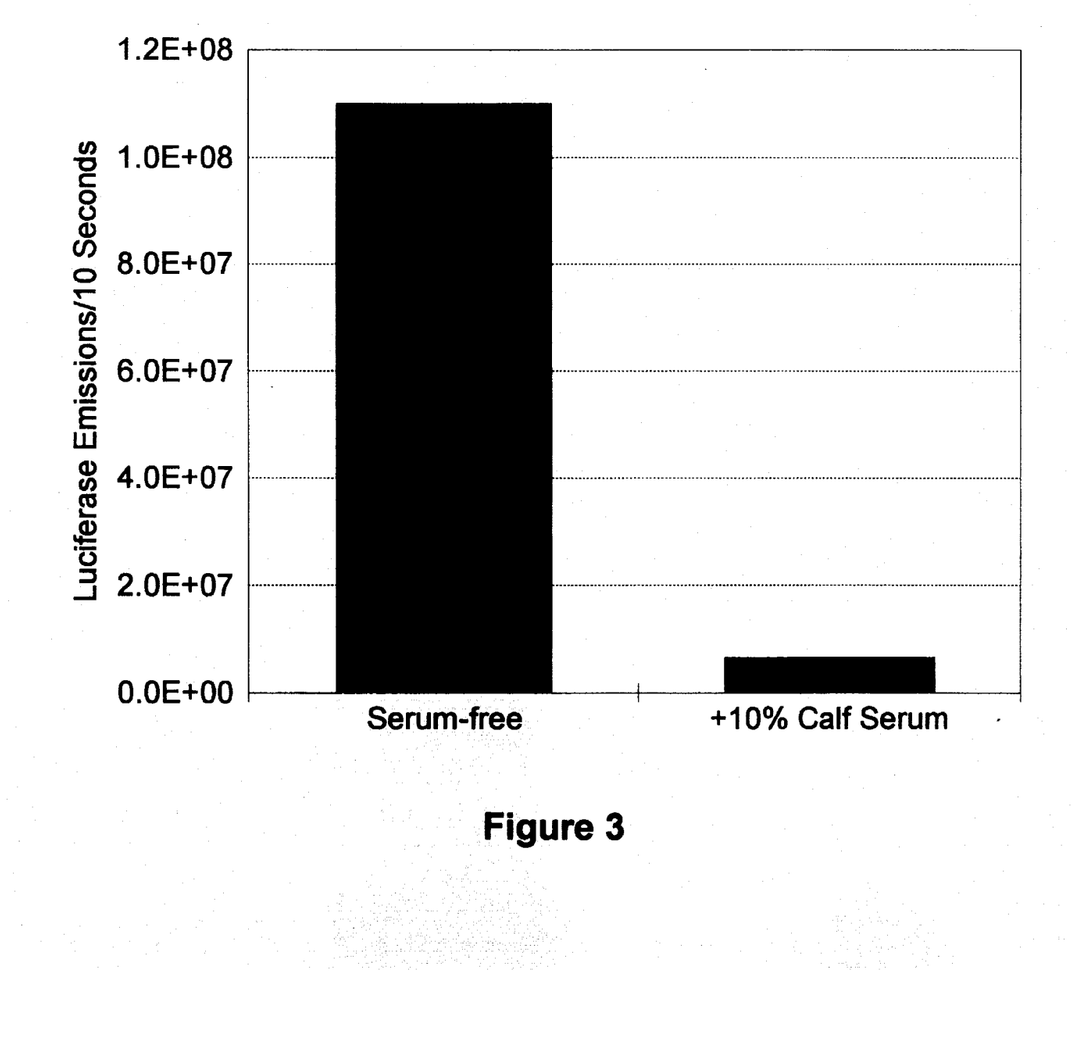
FIG. 3 is a graph showing the effects of serum on PolyGum (MLV) mediated transfection of NIH 3T3 cells.

The effects of serum on PolyGum (MLV) mediated transfection of NIH 3T3 cells is illustrated in FIG. 3. Under these transfection conditions, greatly increased transfection is found with serum-free conditions than in the presence of 10% calf serum. Under other transfection conditions, little change is noted with serum transfection.

Figure 4:
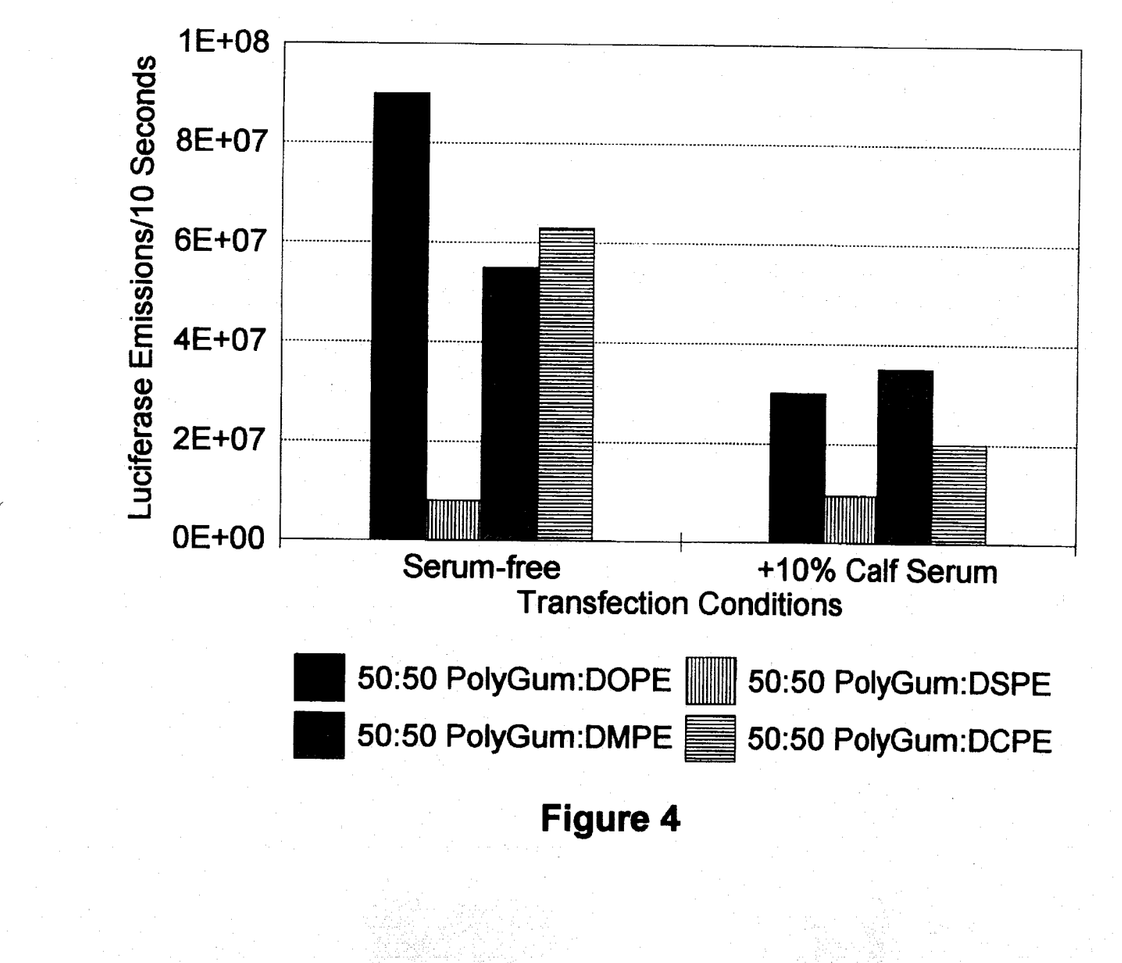
FIG. 4 is a graph depicting the influence of phosphatidylethanolamine (PE) side chain structure on transfection of NIH 3T3 cells using a 50:50 mixture of the PE derivatives and PolyGum in the presence of 10% calf serum and without serum.
Figure 5:
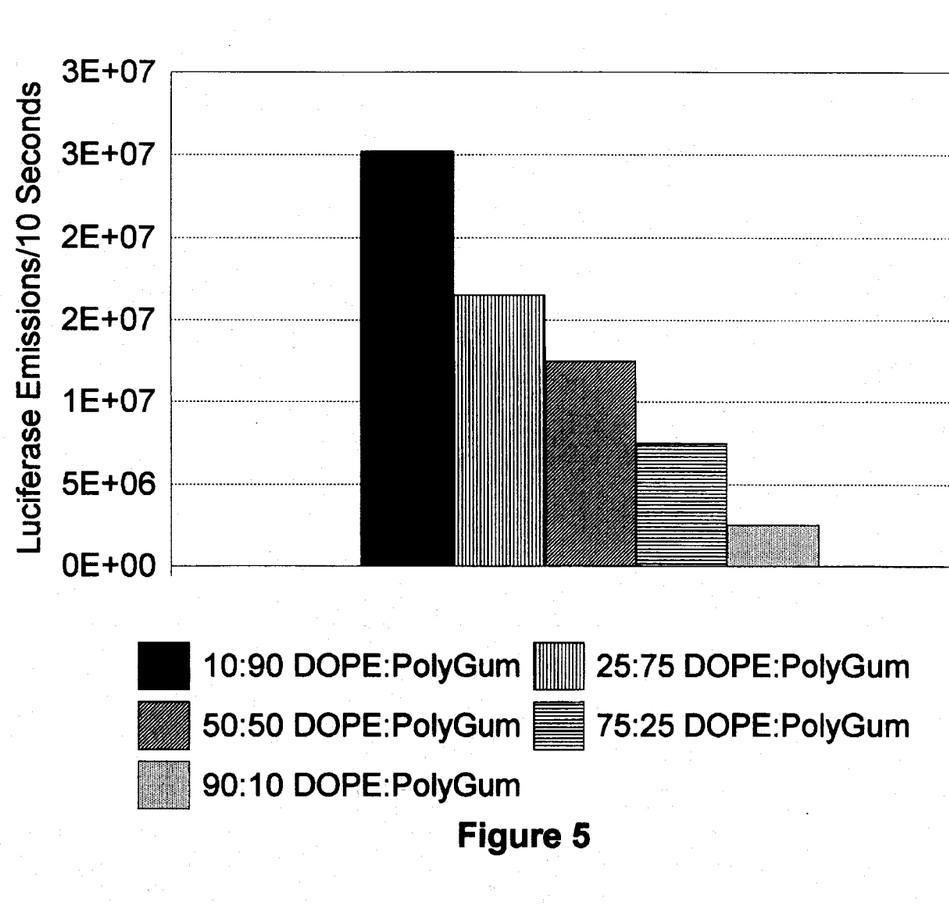
FIG. 5 is a graph showing the optimization of the mole ratio of DOPE to PolyGum (SV) in serum-free transfection of NIH 3T3 cells.

FIG. 4 plainly demonstrates how transfection of cells is influenced, with and without serum, by the side chain characteristics of the phosphatidylethanolamine utilized to generate the vesicles. The 50:50 PolyGum:DOPE formulation is superior for serum-free transfection, while the 50:50 PolyGum:DMPE formulation prevails in the serum added case.

As the mole ratio of DOPE to Polygum in SVs is increased (See FIG. 5), the efficiency of transfection is lowered in a generally linear fashion.

Figure 6:
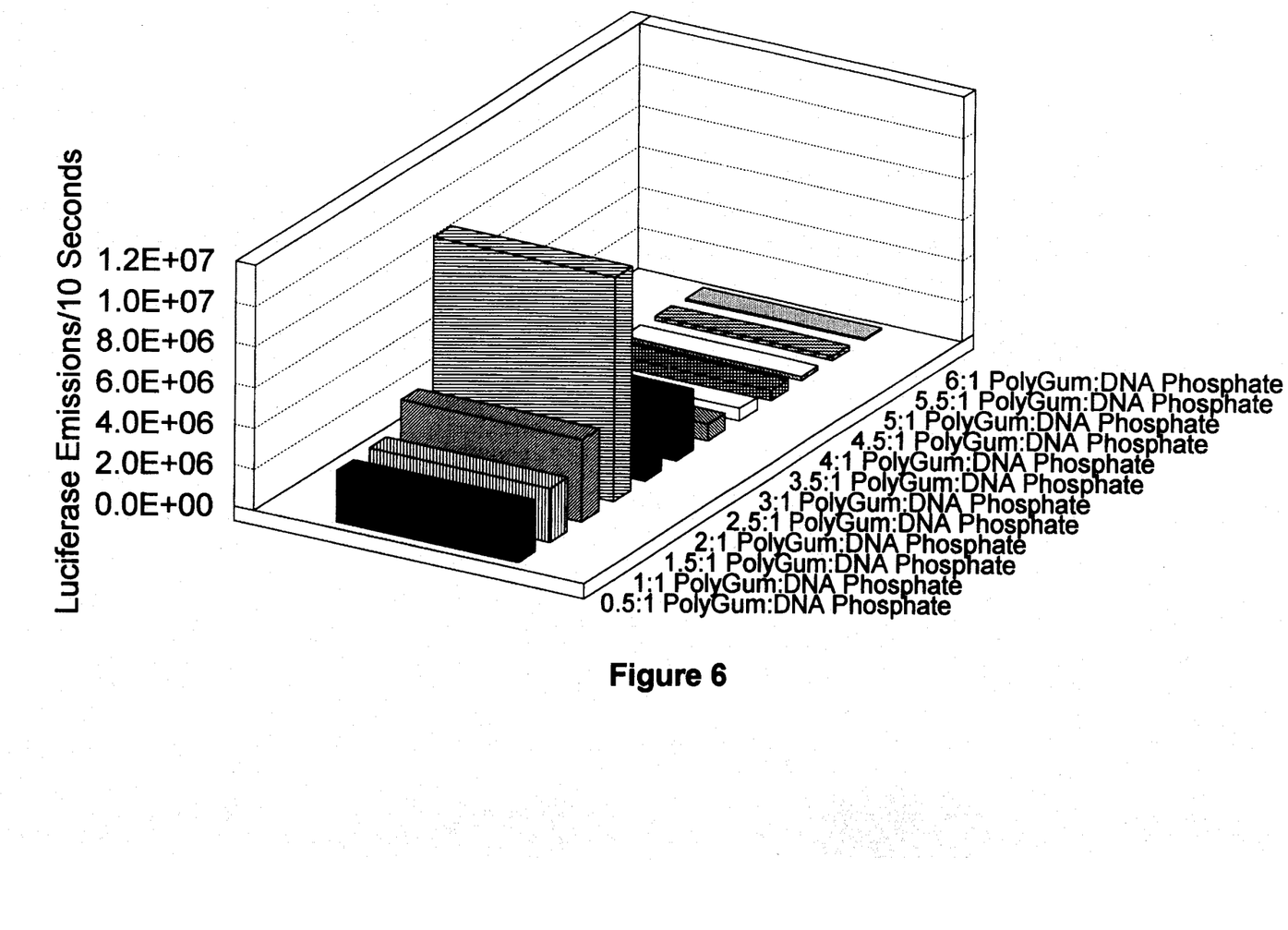
FIG. 6 is a graph illustrating the optimization of the charge ratio of PolyGum (SV) to DNA in serum-free transfection of NIH 3T3 cells.

For PolyGum containing SVs, FIG. 6 shows the DNA charge ratio optimization data. For the ranges presented, clearly, a 2:1 PolyGum:DNA phosphate ratio maximizes transfection.

Figure 7:
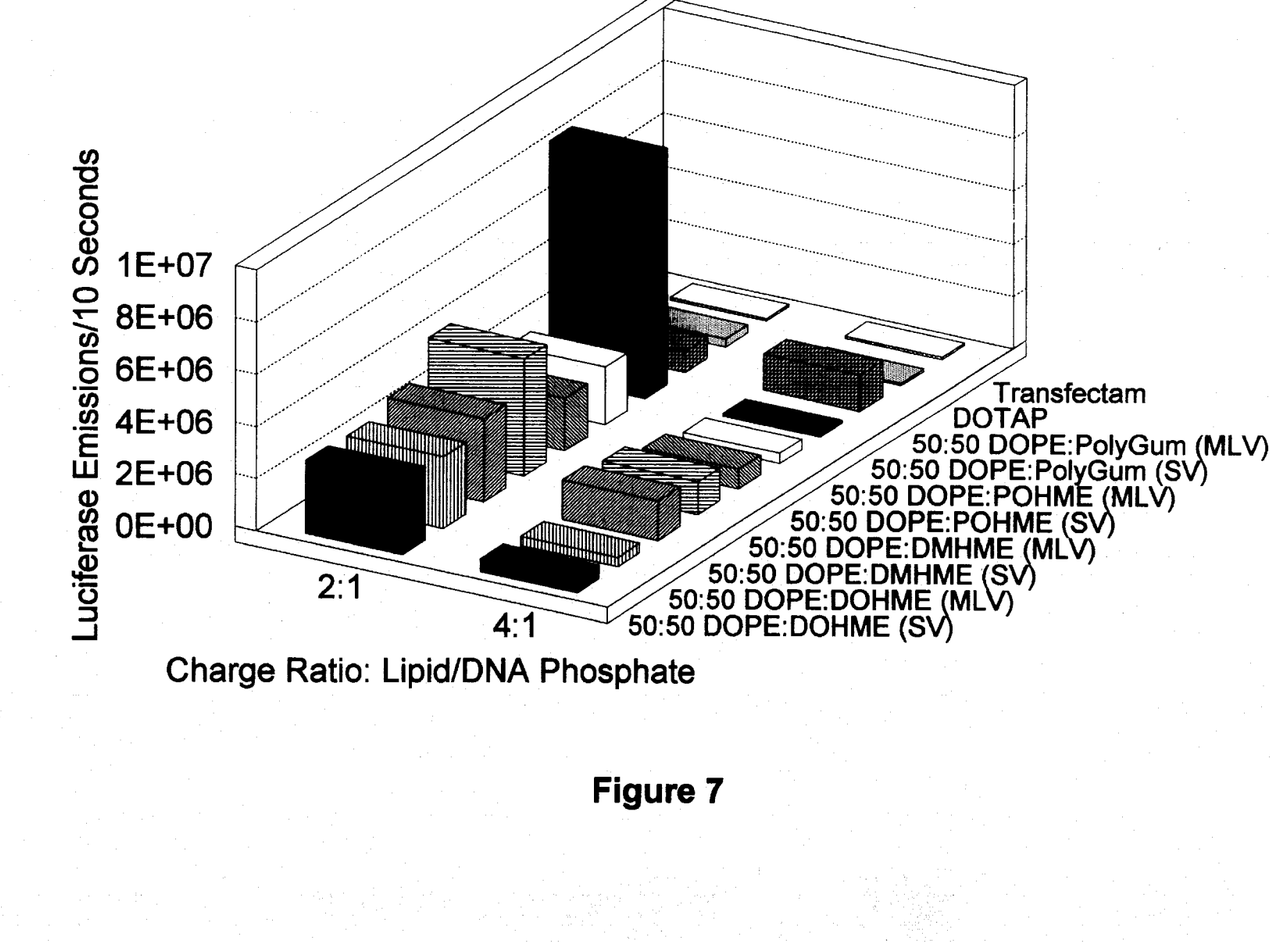
FIG. 7 is a graph portraying an efficiency comparison of utilized cationic lipids in the serum-free transfection of DU-145 cells.
Figure 8:
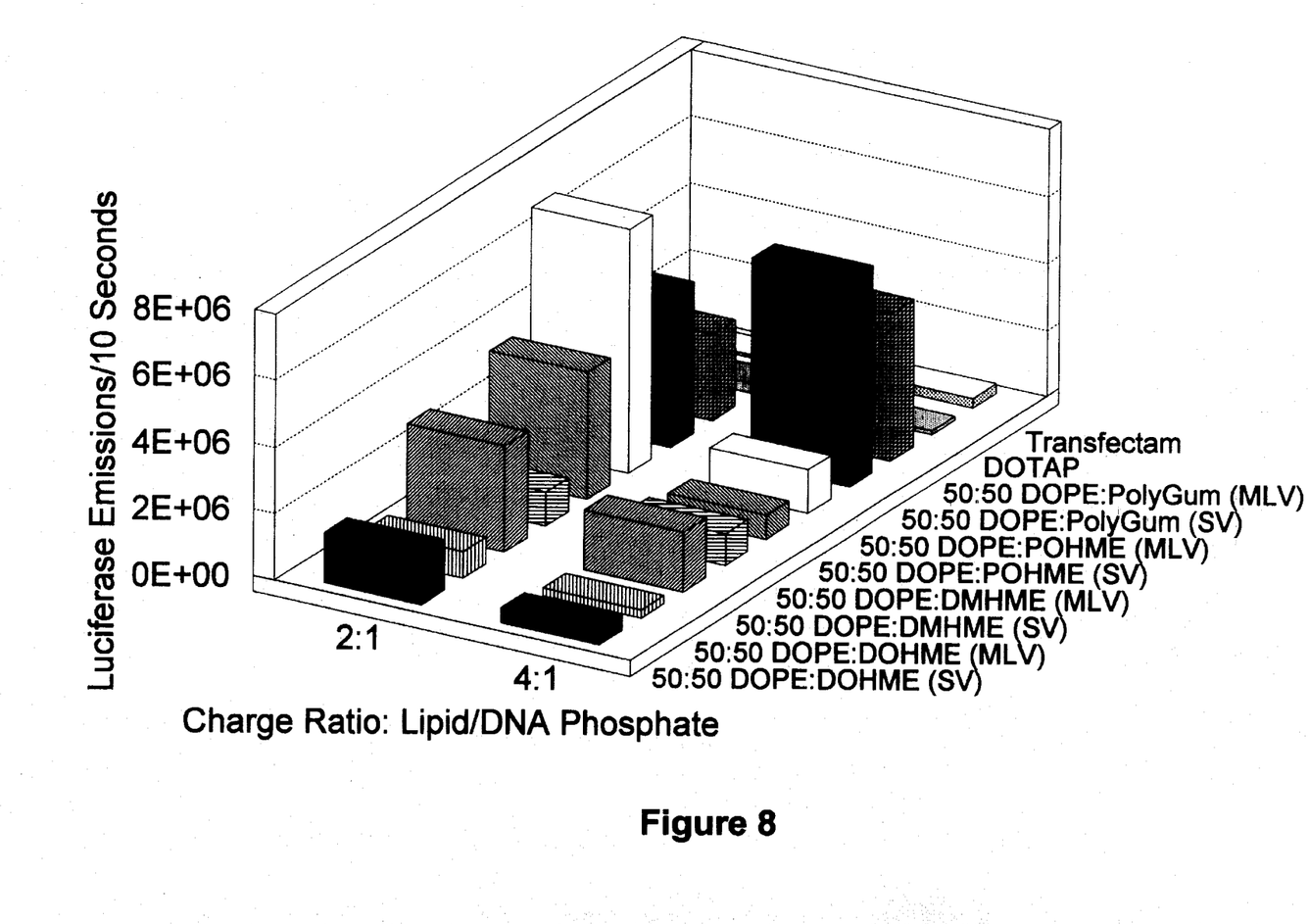
FIG. 8 is a graph showing an efficiency comparison of utilized cationic lipids in transfection of DU-145 cells in the presence of 2% FBS.

As seen in FIGS. 7 and 8, the presence of 2% FBS alters, as compared with serum-free conditions, the transfection levels for different formulations. Without serum, and at a 2:1 lipid to DNA phosphate ratio, the 50:50 DOPE:PolyGum (SV) formulation is most efficient for transfection. With serum, at the 2:1 ratio, the 50:50 DOPE:POHME (MLV) formulation is most efficient, however, the 50:50 DOPE:PolyGum species is second highest in efficiency of transfection. At the 4:1 ratio with serum the 50:50 DOPE:PolyGum (SV) formulation is once again the most efficient transfection agent, with the MLV 50:50 DOPE:PolyGum composition in second. Distinctly, the PolyGum reagent is a useful agent for transfecting cells.

Toxicity of the subject compounds was evaluated by application of the standard Alamar Blue toxicity procedure. The results indicate less toxicity for both PolyGum MLV and SV formulations than for LIPOFECTIN™ and several other amine containing vesicles.

EXAMPLES

Example 1

Chemicals

Dioleoylphosphatidylethanolamine was purchased from Avanti Polar Lipids Inc. (Birmingham, Ala.). Lipofectamine was obtained from Life Technologies. A liposome preparation containing DOTAP was obtained from Boehringer Mannheim. Cholesterol was purchased from Sigma Chemical Company (St. Louis, Mo.). Alamar blue was obtained from Alamar Biosciences (Sacramento, Calif).

Example 2

Synthesis of (±)-2,3-Dihydroxy-1,4-[N,N'-bis (2-tert-butyl-diphenylsilyloxyethyl)-N,N'-dimethyl]butanediamine (see compound 3 in Specific Scheme above)

To a mixture of (±)-1,3-butadiene diepoxide (see compound 2 in Specific Scheme above)(0.93 g, 12.0 mmol) and lithium perchlorate (5.09 g, 47.8 mmol) in absolute ethanol (50 mL) was added N-methyl-2-(tert-butyldiphenylsilyloxy) ethylamine (Prepared according to the procedure in: Chaudhary, S. K.; Hernandez, O. Tetrahedron Lett. 1979, 99) (see compound 1 in Specific Scheme above) (15.0g, 47.8 mmol). The reaction mixture was warmed to 60 °C. and allowed to stir for 24 hr. After this time, the reaction solution was allowed to cool to room temperature and then transferred to a separatory funnel containing $Et_2O$ (75 mL). The resultant mixture was washed with saturated aqueous $NaHCO_3$. The organic layer was separated and subsequently washed with $H_2O$ and brine, and then dried ($Na_2SO_4$). The drying agent was filtered and the filtrate was concentrated by rotary evaporation to give the crude product as a yellow oil. Purification was accomplished by $SiO_2$ column chromatography (3% MeOH in $CH_2Cl_2$) to afford 6.96 g (81%) of compound 3(in above Specific Scheme) as an oil.

$R_f$=0.44(10:90 methanol:dichloromethane); $^1$H NMR (300 MHz, $CDCl_3$) δ7.67(m, 8H), 7.39(m, 12H), 3.74(t, J=6 Hz, 4H), 3.64(m, 2H), 2.73–2.58(m, 6H), 2.53(dd, J=4, 13, 2H), 2.32(s, 6H), 1.04(s, 18H);$^{13}$C NMR (75 MHz, $CDCl_3$) δ135.3, 133.3, 129.6, 127.6, 68.6, 61.5, 60.7, 59.6, 42.9, 26.7, 19.0; IR (KBr)3420, 2931, 1112 cm$^{-1}$.

Example 3

Synthesis of (±)-2,3-Dioleoyloxy-1,4-[N,N'-bis(2-tert-butyldiphenylsilyloxyethyl)-N,N'-dimethyl]butanediamine (see compound 4 in Specific Scheme above)

To a mixture of diamine compound 3 (4.26 g, 5.97 mmol), triethylamine (1.83 mL, 13.1 mmol), and 4-dimethylaminopyridine (0.146 g, 1.19 mmol) in $CH_2Cl_2$(30 mL) at 0 °C. was added dropwise oleoyl chloride (3.954g, 13.14 mmol). On complete addition, the reaction mixture was allowed to stir at 0 °C. for 4 hr. whereupon an additional portion of $CH_2Cl_2$(20 mL) was added. The reaction mixture was then transferred to a separatory funnel and the organic layer was washed successively with saturated aqueous $NaHCO_3$, $H_2O$, and brine. The organic layer was dried ($Na_2SO_4$), filtered, and the filtrate solvent removed in vacuo. The crude product so obtained was purified by $SiO_2$ column chromatography (1% MeOH in $CH_2Cl_2$) to yield 4.21 g (57%) of compound 4 as an oil.

$R_f$=0.31(1:99 methanol:dichloromethane); $^1$H NMR (300 MHz, $CDCl_3$)δ7.66(m, 8H), 5.35(m, 4H), 5.15(m, 2H), 3.68 (t, J=6 Hz, 4H), 2.59(t, J=6 Hz, 4H), 2.49(m, 4H), 2.27–2.22(m, 10H), 2.01(m, 8H), 1.28(m, 48H), 1.04(s, 18H), 0.89(t, J=7 Hz, 6H); $^{13}$C NMR (75 MHz, $CDCl_3$) δ 172.8, 135.4, 133.6, 129.9, 129.8, 129.6(2), 129.4, 128.5, 127.5, 70.0, 62.2, 59.7(2), 58.1, 43.0, 34.2, 31.8, 29.7, 29.4, 29.3, 29.2, 29.1, 29.0, 27.1(2), 26.7, 24.9, 22.6, 19.0, 14.0; IR (KBr) 2927, 1733.2, 1112 cm$^{-1}$.

Example 4

Synthesis of (±)-2,3-Dioleoyloxy-1,4-[N,N'-bis (2-hydroxyethyl)-N,N'-dimethyl]butanediamine (see compound 5 in Specific Scheme above)

To a solution of diamine compound 4(4.21 g, 3.39 mmol) in THF (10 mL) at 0° C. was added dropwise a solution of tetrabutylammonium fluoride (20.4 mL of a 1M solution in THF, 20.4 mmol). The reaction was stirred at 0° C. for 15h at which time analysis by thin layer chromatography revealed that no starting material was present. The reaction mixture was diluted with $CH_2Cl_2$(20 mL) and quenched by addition of saturated aqueous $NaHCO_3$(50 mL). The organic layer was separated and washed successively with $H_2O$ and brine, and dried ($Na_2SO_4$). After filtration, the organic layer was concentrated by rotary evaporation to give the crude product as a yellow oil. The crude product was passed through a short column of silica gel using 5% MeOH in $CH_2Cl_2$as the eluent to obtain a mixture of products. A second chromatographic step using $SiO_2$ column chromatography (5% MeOH in $CH_2Cl_2$) afforded 2.00 g (77%) of 5 as an oil.

$R_f$=0.48(5:95 methanol:dichloromethane); $^1$H NMR (300 MHz, $CDCl_3$) δ5.33(m, 6H), 5.62(s, 2H), 3.55(t, J=5 Hz, 4H), 2.61–2.50(m, 8H), 2.37(t, J=8 Hz, 4H), 2.28(s, 6H), 1.98(m, 8H), 1.63(m, 4H), 1.28(m, 48H), 0.87(t, J=5Hz, 6H); $^{13}$C NMR (75 MHz, $CDCl_3$) δ173.3, 129.9, 129.7(3), 129.5, 129.4, 69.5, 69.4, 59.7, 59.6, 59.5 (2), 58.6, 57.8, 42.3, 34.2, 34.0, 31.8, 29.6(2), 29.4, 29.2 (2), 29.1, 29.0, 27.1, 27.0, 26.8, 24.8, 22.5, 22.4, 14.0, 13.9; IR (KBr) 3447, 2925, 1739, 1512 cm$^{-1}$.

Example 5

(±)-N,N,N',N'-tetramethyl-N,N'-bis(2-hydroxyethyl)- 2,3-di(oleoyloxy)-1,4-butanediaminium iodide (see compound 6, which is PolyGum, in Specific Scheme above)

A 25 mL round bottom flask was charged with diaminodiol compound (1.26 g, 1.65 mmol) and methyl iodide (16.5 mL, 265 mmol). The solution was stirred at ambient temperature for 24 hr. After this time, the methyl iodide was evaporated with the assistance of a steady stream of nitrogen gas (note: this operation must be performed in a fume hood). The residue obtained on removal of the methyl iodide was doubly recrystallized from acetonitrile to give 0.40 g (23%) of compound 6 as a white powder (mp 169°–171° C.

$R_f$=0.28(5:95 methanol:dichloromethane); $^1$H NMR (300 MHz, $CDCl_3$) δ5.60(m, 2H), 5.33(m, 4H), 4.53(m, 8H), 3.47(s, 6H), 3.42(s, 6H), 2.50(m, 4H), 2.00(m, 8H), 1.65(m, 4H), 1.29(m, 44H), 0.88(t, 6H); IR (KBr)3355, 2901, 1753, 1467 cm$^{-1}$. The analytical calculation for $C_{48}H_{94}I_2N_2O_6$ is: C=54.96; H=9.03;and N=2.67 and the found amounts were: C=54.78; H=9.04; and N=2.63.

Example 6

Tissue Culture and Plasmids

NIH 3T3 cells were grown in Dulbecco's modified Eagles medium (DMEM)+10% fetal calf serum. The DNA plasmid pCMVL was prepared by standard methods and used as a 369 ng/ μl solution in TE, pH=7.6. The luciferase reporter plasmid pCMVL was prepared at UC Davis, and consists of the P. pyralis luciferase cDNA subcloned into the plasmid pRc/CMV (Invitrogen).

Example 7

Formation of MLVs and SVs

Multilamellar and small sonicated vesicles were prepared by addition of the cationic lipid DOHME together with DOPE, both as solutions in chloroform, to a 5 ml sample vial. The chloroform was removed via rotary evaporation with the water bath set at a constant temperature of 37° C.

The resulting thin lipid films were placed under high vacuum overnight to insure that all traces of solvent had been removed. The lipid mixture was resuspended using distilled water (2 mmole total lipid/1 ml water) and vortex mixed to give a suspension of MLVs. This cloudy suspension was sonicated for fifteen minutes using a bath sonicator until a clear suspension containing SVs was obtained.

Example 8

Formation of Liposome/DNA Complexes

Sequential addition of DMEM (with or without 10% fetal calf serum), pCMVL plasmid (for n=4, 4 μg), and liposome formulation into a 2 ml Eppendorf tube gave a total volume of 800 μl. The relative amount of liposome:pCMVL plasmid used was determined by the desired cationic lipid:DNA phosphate charge ratio. The mixing of these substances was followed by thorough vortexing.

Example 9

Transfection of NIH 3T3 Cells 24 well tissue culture plates containing $5.0 \times 10^4$ cells/well rapidly dividing adherent NIH 3T3 cells per well were transfected. The growth media was removed via aspiration and the cells were washed once with 0.5 ml PBS/well. A 200 μl aliquot of liposome-DNA complex was added to each well and the cells were allowed to incubate for 4 hr. at 37° C. If desired, at this time, 1 ml of DMEM +10% fetal calf serum/well was added and the cells were allowed to incubate for an additional 48 hr, after which assays of toxicity and/or efficacy were performed. Equivalent procedures were utilized for the DU-145 cells.

Example 10

Determination of Relative Luciferase Light Emissions

Transfection activity was measured using the luciferase assay. Luciferase assays were performed with a luciferase assay kit (purchased from Analytical Luminescence Laboratories) using a Monolight 2010 luminometer (Analytical Luminescence Laboratories, San Diego, Calif.) according to the manufacturer's instructions. The media was removed from the transfected cells via aspiration. 0.5 ml of luciferase buffer/well was added, and the cells were placed on ice for 15 min. Luciferase light emissions from 100 μl of the lysate were measured using the luminometer.

Example 11

Alamar Blue Toxicity Assay

Alamar blue (Alamar Biosciences, Sacramento, Calif.), was diluted in cell culture media to 10%, added to cells, and incubated for up to two hours. Reduced dye was quantitated using a CytoFluor 2300 fluorescence plate reader with a 530 nm excitation filter and a 590 nm emission filter. Values expressed represent fluorescence less background. The same transfected cells can subsequently be assayed for reporter protein activity after Alamar Blue analysis.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A compound having the structure:

wherein

R is fatty acid alkyl or fatty acid alkenyl group and

$X^-$ is an anion.

2. A compound according to claim 1, wherein R is

—$CH_2(CH_2)_6CH$=$CH(CH_2)_7CH_3$.

3. A compound according to claim 1, wherein $X^{31}$ is a halide.

4. A compound of matter having the structure:

* * * * *